United States Patent
Kikkeri

(10) Patent No.: US 11,006,856 B2
(45) Date of Patent: May 18, 2021

(54) METHOD AND PROGRAM PRODUCT FOR MULTI-JOINT TRACKING COMBINING EMBEDDED SENSORS AND AN EXTERNAL SENSOR

(71) Applicant: Harshavardhana Narayana Kikkeri, San Jose, CA (US)

(72) Inventor: Harshavardhana Narayana Kikkeri, San Jose, CA (US)

( * ) Notice: Subject to any disclaimer, the term of this patent is extended or adjusted under 35 U.S.C. 154(b) by 248 days.

(21) Appl. No.: 15/371,397

(22) Filed: Dec. 7, 2016

(65) Prior Publication Data
US 2017/0332946 A1 Nov. 23, 2017

Related U.S. Application Data

(60) Provisional application No. 62/337,337, filed on May 17, 2016.

(51) Int. Cl.
*A61B 5/11* (2006.01)
*G16H 20/30* (2018.01)
(Continued)

(52) U.S. Cl.
CPC ............. *A61B 5/11* (2013.01); *A61B 5/0476* (2013.01); *A61B 5/1114* (2013.01); *A61B 5/1116* (2013.01); *A61B 5/1123* (2013.01); *A61B 5/1127* (2013.01); *A61B 5/14532* (2013.01); *A61B 5/4528* (2013.01); *A61B 5/742* (2013.01); *A61B 5/7405* (2013.01); *G16H 20/30* (2018.01); *G16H 40/63* (2018.01); *A61B 5/0022* (2013.01); *A61B 5/1118* (2013.01); *A61B 5/6805* (2013.01);
(Continued)

(58) Field of Classification Search
CPC ....... A61B 5/11; A61B 5/1114; A61B 5/1116; A61B 5/1123; A61B 5/4528
See application file for complete search history.

(56) References Cited

U.S. PATENT DOCUMENTS

| | | | | |
|---|---|---|---|---|
| 6,152,890 A | * | 11/2000 | Kupfer | A61B 5/103 600/595 |
| 6,692,447 B1 | * | 2/2004 | Picard | A61B 5/103 600/587 |

(Continued)

OTHER PUBLICATIONS

Macellari, CoSTEL: a computer peripheral remote sensing device for 3-dimensional monitoring of human motion, May 1983, Medical & Biological Engineering & Computing, 21, p. 311-318 (Year: 1983).*

*Primary Examiner* — Daniel L Cerioni
*Assistant Examiner* — Raymond P Dulman
(74) *Attorney, Agent, or Firm* — Hamre, Schumann, Mueller & Larson, P.C.

(57) ABSTRACT

A method and program product includes assigning a first location of at least one embedded device. The embedded device includes at least one sensor and is associated with a one joint capable of movement. The first location is captured by the sensor. A second location of the at least one embedded device is assigned. The second location being captured by observation of the embedded device by at least one external sensor. A pose correspondence between the first location and the second location is established using a model of the joint. The sensor is calibrated by tracking a change in a pose captured by the external sensor and a change in a pose captured by the one sensor as the joint moves.

14 Claims, 9 Drawing Sheets

(51) Int. Cl.
    *G16H 40/63*   (2018.01)
    *A61B 5/00*    (2006.01)
    *A61B 5/0476*  (2006.01)
    *A61B 5/145*   (2006.01)

(52) U.S. Cl.
    CPC ......... *A61B 5/6831* (2013.01); *A61B 2503/10* (2013.01)

(56) References Cited

U.S. PATENT DOCUMENTS

| | | | |
|---|---|---|---|
| 7,725,279 B2* | 5/2010 | Luinge | G06F 3/011 |
| | | | 702/150 |
| 8,657,772 B2 | 2/2014 | Einarsson | |
| 8,702,430 B2 | 4/2014 | Dibenedetto et al. | |
| 2008/0091373 A1* | 4/2008 | McGibbon | A61B 5/1121 |
| | | | 702/95 |
| 2008/0112592 A1* | 5/2008 | Wu | A61B 5/1113 |
| | | | 382/103 |
| 2010/0130893 A1* | 5/2010 | Sankai | A63B 21/4047 |
| | | | 601/5 |
| 2015/0130696 A1* | 5/2015 | Keesling | G06F 3/014 |
| | | | 345/156 |
| 2016/0015972 A1* | 1/2016 | Hyde | H02J 7/025 |
| | | | 607/48 |
| 2016/0198995 A1 | 7/2016 | Yeung et al. | |
| 2016/0202755 A1 | 7/2016 | Connor | |
| 2016/0321841 A1* | 11/2016 | Christen | G06F 3/167 |
| 2017/0188980 A1* | 7/2017 | Ash | A61B 5/744 |
| 2017/0189751 A1* | 7/2017 | Knickerbocker | G09B 19/0038 |

* cited by examiner

METHOD AND PROGRAM PRODUCT FOR MULTI-JOINT TRACKING COMBINING EMBEDDED SENSORS AND AN EXTERNAL SENSOR

CROSS-REFERENCE TO RELATED APPLICATIONS

The present Utility patent application claims priority benefit of the U.S. provisional application for patent Ser. No. 62/337,337 "ACCURATE MULTIJOINT POSE TRACKING BY FUSING EMBEDDED SENSOR INFORMATION WITH EXTERNAL SENSOR INFORMATION" filed 17 May 2016 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

FIELD OF THE INVENTION

One or more embodiments of the invention generally relate to multi joint tracking. More particularly, the invention relates to multi-joint tracking combining embedded sensors and an external sensor.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Various types of sensors including gyroscopes and accelerometers are increasingly being embedded in devices and placed on joints of humans and robots to measure some local information, for example position of joints, velocity of motion, and angles between joints. Typically, sensors require calibration to map raw readings to actual measurements in physical units. External sensors, such as Kinect, capture three dimensional depth and RGB color information.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. A system includes a sensor array which longitudinally spans a body joint in order to measure movement of that body joint. This sensor array can further include a first accelerometer which is proximal to the body joint and a second accelerometer which is distal to the body joint.

By way of educational background, another aspect of the prior art generally useful to be aware of is that a system includes a wearable joint-action sensor that detects actions of a joint that links a first body segment to a second body segment by using a proximity sensor worn on the first body segment to detect a separation between the proximity sensor and the first and/or second body segment.

By way of educational background, another aspect of the prior art generally useful to be aware of is that a system includes a wearable device having feedback characteristics including a compliant article arranged to extend over an anatomical portion of a wearer and for providing a user with information regarding range of motion parameters of a joint and/or to condition users to maintain proper joint orientations. Sensors provided with the wearable device detect the orientation of the joint and send signals to a processor for analysis.

By way of educational background, another aspect of the prior art generally useful to be aware of is that a system for monitoring joint position following introduction of a joint prosthesis in a patient includes a first angular movement sensor positioned adjacent a first side of a bodily joint of a patient and a second angular movement sensor positioned adjacent a second, opposite side of the bodily joint. A receiver can receive data from the angular movement sensors.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIG. 8a show an external view. FIG. 8b shows an internal view.

Figure 1:
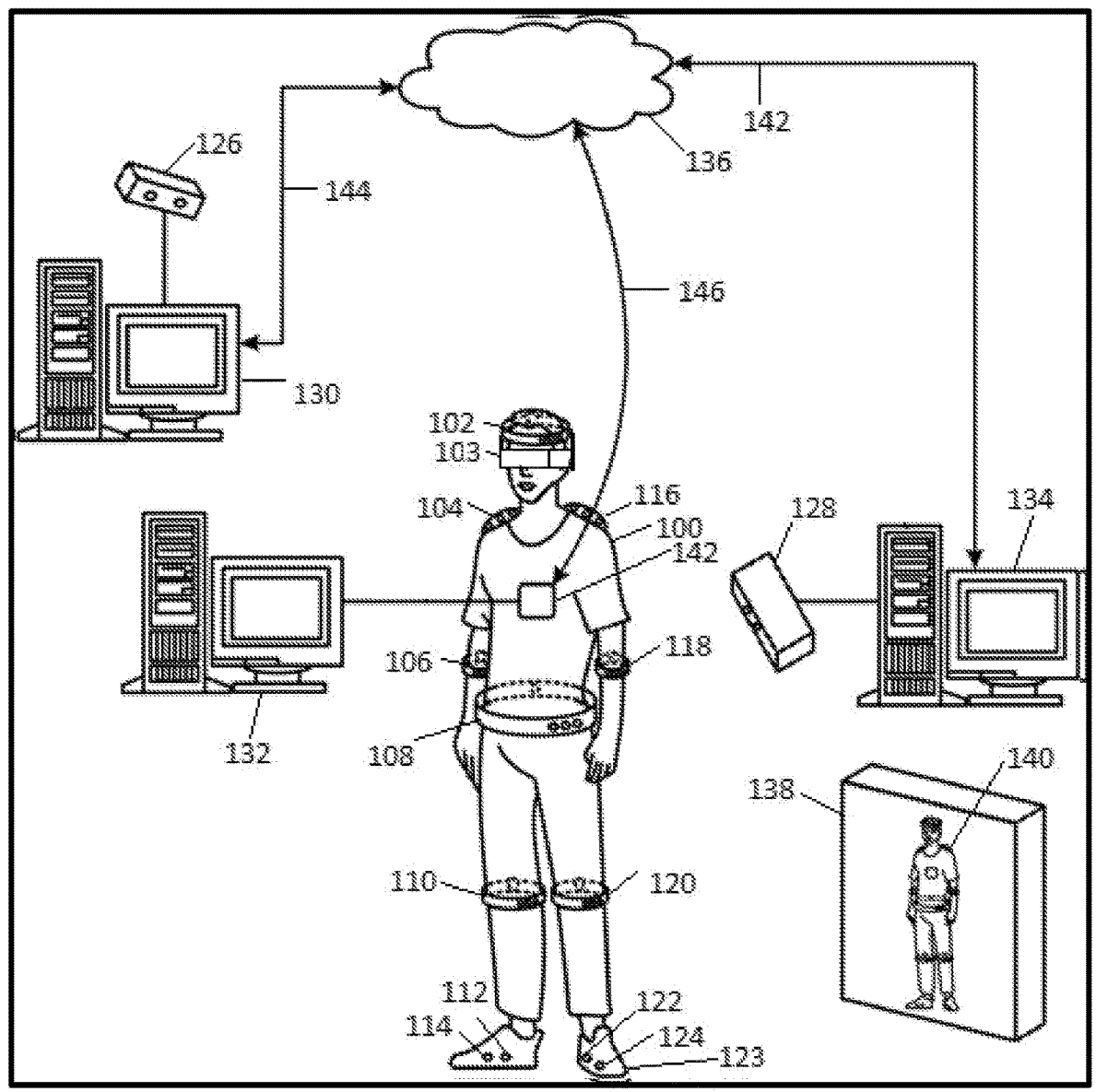
FIG. 1 illustrates an exemplary system for combining external sensors and embedded sensors, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See *In re Frye*, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology

The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn. 112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter. Moreover, for any claim of the present invention which claims an embodiment "consisting essentially of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Additionally, the phrase "configured to" or "operable for" can include generic structure (e.g., generic circuitry) that is manipulated by software and/or firmware (e.g., an FPGA or a general-purpose processor executing software) to operate in a manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

Some embodiments of the present invention, and variations thereof, may provide methods to combine global information from external sensors with local information from embedded sensors to enable one time as well as continuous calibration of embedded sensors using external sensors. Examples of embedded sensors may include but are not limited to gyroscope sensors, magnetometers, accelerometers, compass, bend sensors, angle sensors, flex sensors, or passive sensors like QR codes or fiduciary markers or Infra-Red dots, RGB sensors which detect motion through optical flow, stereoscopic sensors, infra depth sensors which detect motion etc. The sensors could be embedded on clothing or other attachments on the joints (either human skeletal joints like arms, wrists, fingers, thighs, ankles, foot, toes, legs, lower back or robotic joints like linear joints, angular joints). Examples of external sensors are Time of Flight depth sensors like Microsoft Kinect One™, 2D and 3D laser sensors, thermal sensors, RGB sensors, infra-red sensors, multispectral sensors, and stereoscopic sensors, Mixed Reality sensors like Microsoft HoloLens™, Virtual Reality Sensors like HTC Vive™ Google DayDream™, Sony PlayStation VR™, Samsung Gear VR or Augmented Reality sensors like Google Tango™, Stereoscopic glasses like Snap Spectacles™. Note that the external sensor may not track all the joints tracked by the embedded sensors. As long as there is a way to infer the motion of a joint with embedded sensor with information from the external sensor, we can use it to establish correspondence. Some embodiments may enable spatial correspondence between different embedded sensors to be established, which may be used to extract relative information between embedded sensors and their corresponding measurements. In some embodiments, significant value may be added by being able to track, correlate and infer from the embedded sensors. Once the spatial correspondence has been initially established, the tracking may continue even when the subject human or joint is not in view of the external sensor. Some embodiments may enable determining range of motion of joints and length of the joints. The human may begin with elbow straight and bend the elbow completely. By having embedded sensors in the palms and/or bend sensors on the elbows and/or observing the motion through the external sensor, the full range of elbow motion may be known. This may be used later for detecting accurately virtually any type of action. In a non-limiting example, it may be used to detect a punch action when the elbow is fully bent and then fully stretched. Also having these calibrated embedded sensors such as, but not limited to, gyroscopes, accelerometers, bend sensors, etc. in the elbow and palms, which measure the spatial motion over time, a quality of punch may be determined and a person may be trained to improve their punches over time. Other embodiments may provide a user interface which may allow the user to enter additional information which may be used to improve or derive additional information from the sensor readings. In a non-limiting example, the user may enter their age or previous injuries/surgeries, which may be used to derive the optimal training or warn the user if too much pressure is being applied on a joint which had undergone surgery. In some embodiments, the user interface may also show replay of the sensor data, for example, without limitation, replay a golf shot using data derived from the embedded sensors on a model of the user. In some embodiments, the user interface may also be used to show the time at which an incorrect motion was made and then show the correct and incorrect versions side by side, allowing the person or learning machine to learn. In some embodiments, information from these calibrated sensors may be used to train persons/mechanical joints on, but not limited to, golf shots, baseball swings, baseball throws etc. In other embodiments, the embedded sensor information from the person may be compared to other persons, and may be used to determine a training schedule for the person to follow another person's training. In some embodiments, it may also be used to track collectively, in specific subgroups for example, without limitation, males between the gages of 40-45, or individually the progress in different goals. In a non-limiting example, determining what type of exercises result in maximum weight loss in rib section for women between the ages of 50-54. In some embodiments, it may also be combined with medical data of people to determine what type of exercise regimen may have prevented or increased the rate of a medical condition such as, but not limited to, osteoporosis in women.

External sensors may track the joint absolute poses such as, without limitation, position, velocity, acceleration, etc. when they are visible, but they may not be very accurate and also may not track them when they may not be visible either because they may be covered by loose cloth or because they may be hidden from view. Note that external sensors means anything which tracks the motion of the joint with respect to external reference. So it could be a mounted externally like the Microsoft Kinect One™, RGBD sensors or it could be mounted on the body such as virtual reality or augmented reality or mixed reality headsets like mounted on the head which tracks the head joint motion with respect to the world. Embedded sensors such as, but not limited to, gyroscopes, accelerometers, magnetometers, etc., either individually or in any combination, may track the relative position of joints very accurately, but they may lose track of absolute position very quickly due to drift. Also they may not know the absolute position of the joints and the relative positions between the joints to be able to track them accurately over a period of time. Embodiments of the present invention may provide a device and/or method which may accurately track the overall position of the joints of either a person or a mechanical device such as, but not limited to, a robot arm, leg etc. It is believed that current tracking devices may only crudely measure the motion of one of the joints and try to infer the overall action or joint movement, but often fail. For example, even though a person may be burning a lot of calories when a person is doing yoga, since there is not much gross motion in the legs, many of the current devices fail to register this motion.

Embodiments of the present invention may provide for the determination of the position of the joints very accurately using a combination of external sensors and embedded sensors/actuators herein referred to collectively as embedded devices. Actuators may be devices which provide feedback to the senses, such as but not limited to vibrators, RGB leds, speakers, displays Virtual Reality/Augmented Reality/Mixed reality headsets and glasses, tactile feedback, neural feedback, olfactory feedback, and gustatory feedback. The embedded sensors may be either directly observable to the external sensor, for example, without limitation, a band on the hand which has a visual marking indicates where the sensor is located, or not directly observable, for example, without limitation, an embedded device inside the clothing adjacent to the spinal column. Directly observable may include not just visual observation, but any observation within the electromagnetic spectrum such as, but not limited to, radio frequencies, infra-red, etc. which may localize the position of the embedded devices. In some alternate embodiments, the embedded devices may determine their position relative to a reference position and transmit their location to a receiving device.

In cases where the embedded device may be directly observable, the position of the device with respect to the external sensors may be determined by using techniques of range sensing. In a non-limiting example, infrared range detectors may be used to determine a three dimensional position of the embedded device with respect to a fixed external reference. This external reference may be one of the external sensors or an external display or any arbitrary point in space.

In cases where the embedded device may not be directly observable, it may have been either directly observable at an earlier point in time or it may not be observable at any point in time. In case it may be observable at any point in time, its position with respect to the external reference may be stored and the sensors in the embedded device which track motion may be used to determine its three dimensional position even when it may not be observable. As soon as it may become observable again, its actual position and the tracked position may be compared and the predicted positions may be corrected using energy minimization techniques such as, without limitation, bundle adjustment. This may be used to track the position of the embedded device even before it was first directly observed by subtracting the sensor observed motion.

In cases where the embedded device is not directly observable, fiduciaries may be connected to it in such a manner as to make the fiduciaries directly observable. Based on the location of the fiduciaries, the three dimensional locations of the embedded devices may be calculated. Fiduciaries may be any object which can be detected externally. Example may include, without limitation, QR codes, checkerboard patterns, color codes, and infrared dots.

FIG. 1 illustrates an exemplary system for combining external sensors and embedded sensors, in accordance with an embodiment of the present invention. In the present embodiment, a person 100 may have various embedded devices with sensors to track their positions. A brain activity sensor (electroencephalogram) 102 may be mounted on the head of person 100 measuring the electrical activity of the brain. A Mixed Reality sensor like but not limited to Microsoft HoloLens™, or a Virtual Reality Sensor like but not limited to HTC Vive™, Google DayDream™, Sony PlayStation VR™, Samsung Gear VR or an Augmented Reality sensor like but not limited to Google Tango™, or Stereoscopic glasses like but not limited to Snap Spectacles™ 103 may be mounted on the eyes and/or ears to provide a virtual reality, augmented reality or mixed reality experience. Shoulder mounted inertial measurement sensors 104 and 116 may be, for example, but not limited to, a 3 D gyroscope, 3D accelerometer, 3D magnetometer, compass, GPS, etc. Flex sensors 106 and 118 may be mounted on elbows of person 100. A combination of pressure sensor and inertial measurement units 108 may be mounted on the waist in the form of a belt. Sensors 110 and 120 may measure an electrical firing of muscles of the knees. Pressure and inertial measurement sensors 112, 114, 122 and 124 may be embedded the person's 100 shoes. Sensors 122 and 124 are depicted embedded in show 123. An embedded compute device 142 may collect data from the sensors and actuators and send command and calibration information to them. The actuators are devices that may provide feedback, such as but not limited to vibrators, RGB leds, and speakers.

Depth sensing cameras 126 and 128 may be an RGB-D type camera, such as, but not limited to, a Kinect™ camera used for the Xbox™ video games from Microsoft™ corporation. However, the techniques described herein are not limited to this camera, as any number of other systems may be used to localization of the position of the embedded devices in 2D or 3D. Such cameras may include, but not limited to, depth sensing cameras available from Mesa Imaging AG, SoftKinetic, and others. Many of these cameras may use infrared (IR) or near-IR lasers to project light onto a scene, and calculate the depth map from the detected reflected light using known time-of-flight (TOF) algorithms. Other types of systems may be used in addition to, or instead of, TOF based systems. For example, but not limited to, stereoscopic cameras available from The ImagingSource LLC®, or StereoVision Imaging, Inc., or 3D Lidars like Velodyne® VLP16™ may be used.

Computer devices 130, 132, and 134 may use one or more external sensors of the similar or dissimilar types in conjunction with zero or more fiduciaries attached to the embedded devices to track their position in 3D, or lower dimensions, through time. Computer devices 130, 132, and 134 may use this tracking to calibrate the parameters of the embedded sensors as well as determine their range of motion. They may communicate with each other and to the embedded device computers either through a cloud network computer 136, a local network, or directly. They may determine a relative position of the embedded devices and their associated joints by finding a best fit for a model of the desired, human or mechanical joint(s) to the joint positions determined by the external sensors. In a non-limiting example, a skeletal tracking algorithm by Microsoft Kinect SDK may provide the poses of the joints of humans with respect to the Kinect™ device.

The captured joint model and the embedded devices 140 associated with the joints may be optionally shown to the user on a display 138 and the user may be provided an option to correct all or parts of this association The attached computer may communicate directly with the display, however any other unit that communicates with the attached computer to affect the display. The user may be prompted to move the joints in specific directions and this information may be used for further calibrate the embedded device parameters. In a non-limiting example, the user may be asked to stand still in a neutral position to determine the noise levels in the sensors. Similarly, the user may be asked to raise his hands all the way to the top and this can be used to determine the range of the shoulder mounted inertial measurement sensor. In case of a mechanical joint, it may be asked to perform very precise motions which cover all of its range and a prior knowledge of the commanded motion may be used for further calibrate the sensors. The user may also be shown the updated joint model data and provided the opportunity to optionally correct it. After the calibration and determination of embedded device position related to the joints, they may be stored either locally on the computers 130, 132, and 134, or stored on the cloud network storage 136 or on the embedded compute device 142 or in any combination of the above. Each of the computers can communicate either locally or through the cloud with each other either before, during or after calibration. Calibration may be done jointly by having the computers communicate with each other and correct for any individual errors of external sensors by fusing information between multiple external sensors. In another embodiment, calibration may also be done individually for each external sensor. The external sensor may be located at multiple geolocations and may communicate with local computers or directly send the information to the cloud. The arrow between the computers and the cloud is a standard way of indicating that the computers communicate with the cloud, as well as with each other in bidirectional fashion. The cloud itself may have a series of servers or storage devices. The software for calibration, modeling may be in the embedded computer, external computer, cloud or any combination of the these In some embodiments, the calibration may be done without using the external devices, if the position of the embedded sensors on the model are known or may be calculated. In a non-limiting example, if the length of the limbs of the person are known and the shoes are on the feet and brain sensors are on the head and the distance between the leg and the head of the person is known, then the person may be asked to stand straight and the embedded sensors may be calibrated with each other. Similarly, other sensors can be calibrated with each other. In other embodiments, if the embedded sensors have a mechanism such as, but not limited to, gyroscopes, accelerometers, magnetometers, barometers, flex sensors, bend sensors, RGB sensors, stereoscopic sensors, infrared sensors, sonars, and range detectors. to indicate their 3D position relation to each other or to an external reference such as, but not limited to, a ground plane, this may be used to perform the calibration and skip the need for external sensors.

Figure 2:
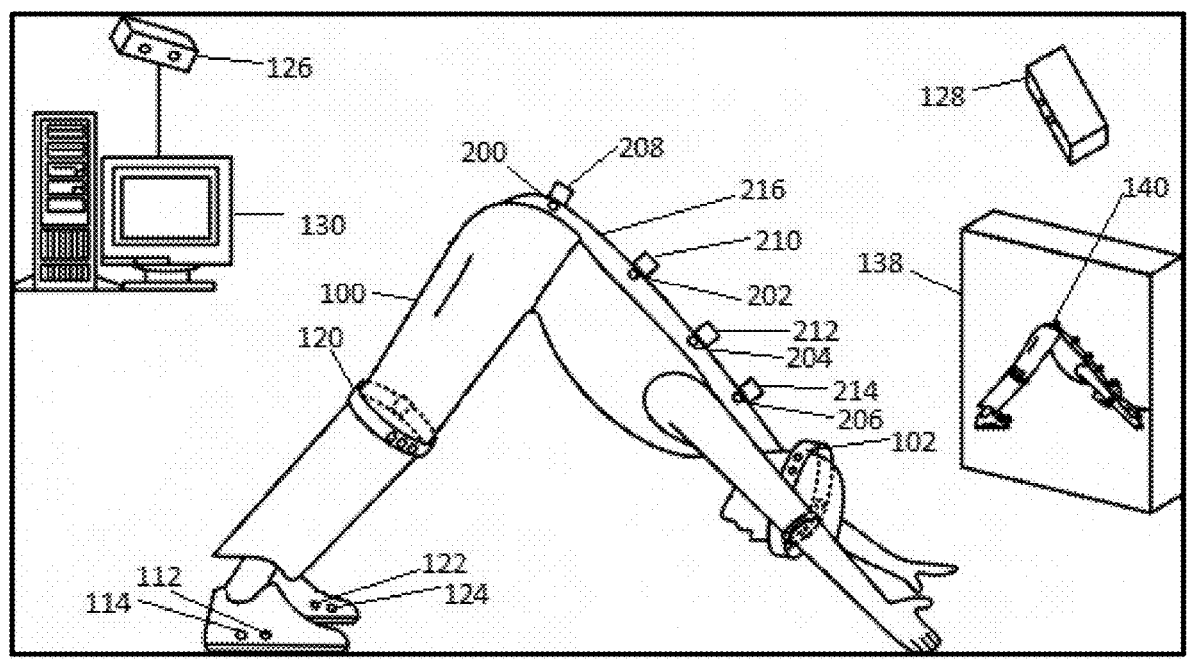
FIG. 2 illustrates an exemplary tracking of joints, in accordance with an embodiment of the present invention.

FIG. 2 illustrates an exemplary tracking of joints, in accordance with an embodiment of the present invention. In the present embodiment sensors were calibrated when person 100 was standing and have been tracking the movement of the joints as the person transitions to this downward dog yoga pose. One or more flex sensors 216 on the back may be determining the amount of flex occurring in the spinal column. The embedded devices 200, 202, 204 and 206 may be tracking the curvature of the spinal column. If optional external sensor(s) 126 and 128 may be available and the attached fiduciaries 208,210, 212 and 214 may be observable through these external sensors, the tracked position of the embedded devices and through them the tracking of joint positions may be further refined. As the joint positions are tracked through time, other moments like, but not limited to, velocity and acceleration of various joints with respect to a reference or with respect to each other may be tracked. These tracked joint positions may be applied the model of the joint and shown back to the user as 140 on display 138. Additionally, this tracked information may be used to provide feedback to the user as to which part of the joint may be incorrectly positioned either automatically by programming the desired joint positions, or by another human who is watching this joint model data either locally or remotely.

Figure 3:
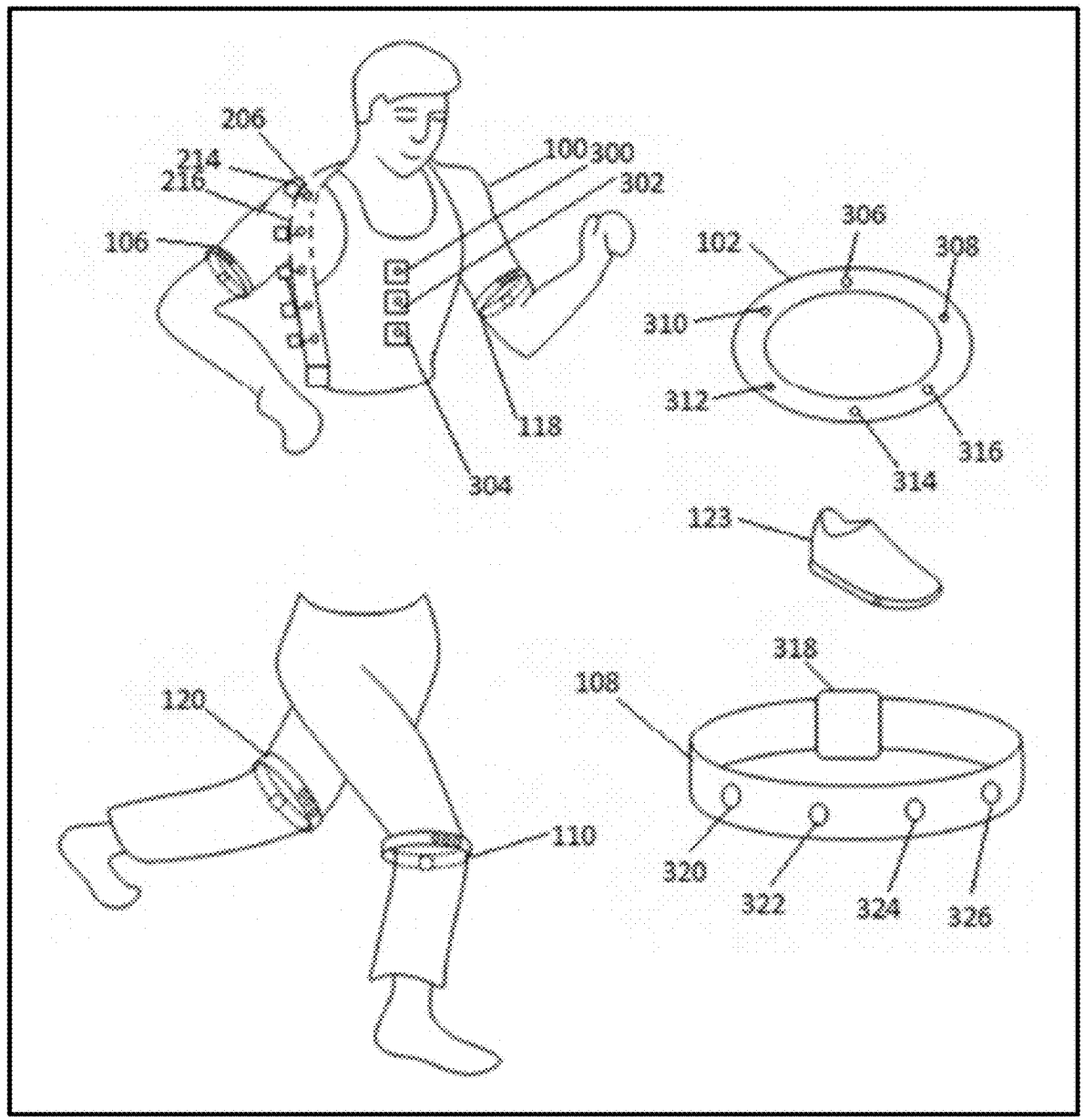
FIG. 3 illustrates exemplary breath sensors, in accordance with an embodiment of the present invention.

FIG. 3 illustrates exemplary breath sensors, in accordance with an embodiment of the present invention. Embedded breath sensors 300, 302, and 304 on a person 100. It is believed that the quality, intensity and timing of airflow via breath may be very important in some activities like, but not limited to, yoga and this information may be correlated with, but not limited to, the type, length, rigor as well as sequence of exercise done to determine if there may be certain patterns which may be more beneficial in this or other regards. Range of motion of the joints may be another metric which may be used to determine the effect a particular exercise regimen or nutritional diet may be having on the person. In other embodiments, for a mechanical joint, a maintenance may be scheduled if it is not able to move the joints to the desired ranges measured by this method. Also, the quality of maintenance or type of lubrication may be rated and measured over a long time using this method. Brain wave sensor 102 may sense different types of waves emitted by the brain. Sensors 306, 308, 310, 312, 314 and 316 may be used to determine whether the brain has entered a particular state for example, without limitation, low frequency alpha state when certain joints were moved in specific waves. This may help people who are trying to meditate to determine the type(s) of poses which may be more likely to induce these states.

Belt sensor 108 worn around the waist of person 100 may have different sensors and actuators. In non-limiting example, actuators 320 and 326 may be used to give feedback to the user to twist more towards left by vibrating 320 or more toward right by vibrating 326. Sensors 322 and 324 may be used to determine the current twist. Pressure sensor 318 may be used to determine a pressure being applied to the abdominal region. This may useful for determining whether a desired pressure is being applied to a correct organ or if there may be undue pressure being applied to a wrong organ. It is believed that in yoga, the relative pressure applied to the abdomen and sacral regions may be very important for practicing Bandhas or locks such as, but not limited to, Mula Bandha or Uddiyana Bandha. Embedded devices 106 and 118 may be mounted on the elbows as shown in FIG. 1 and embedded devices 120 and 110 may be mounted on the knees as shown in FIG. 1.

Figure 4:
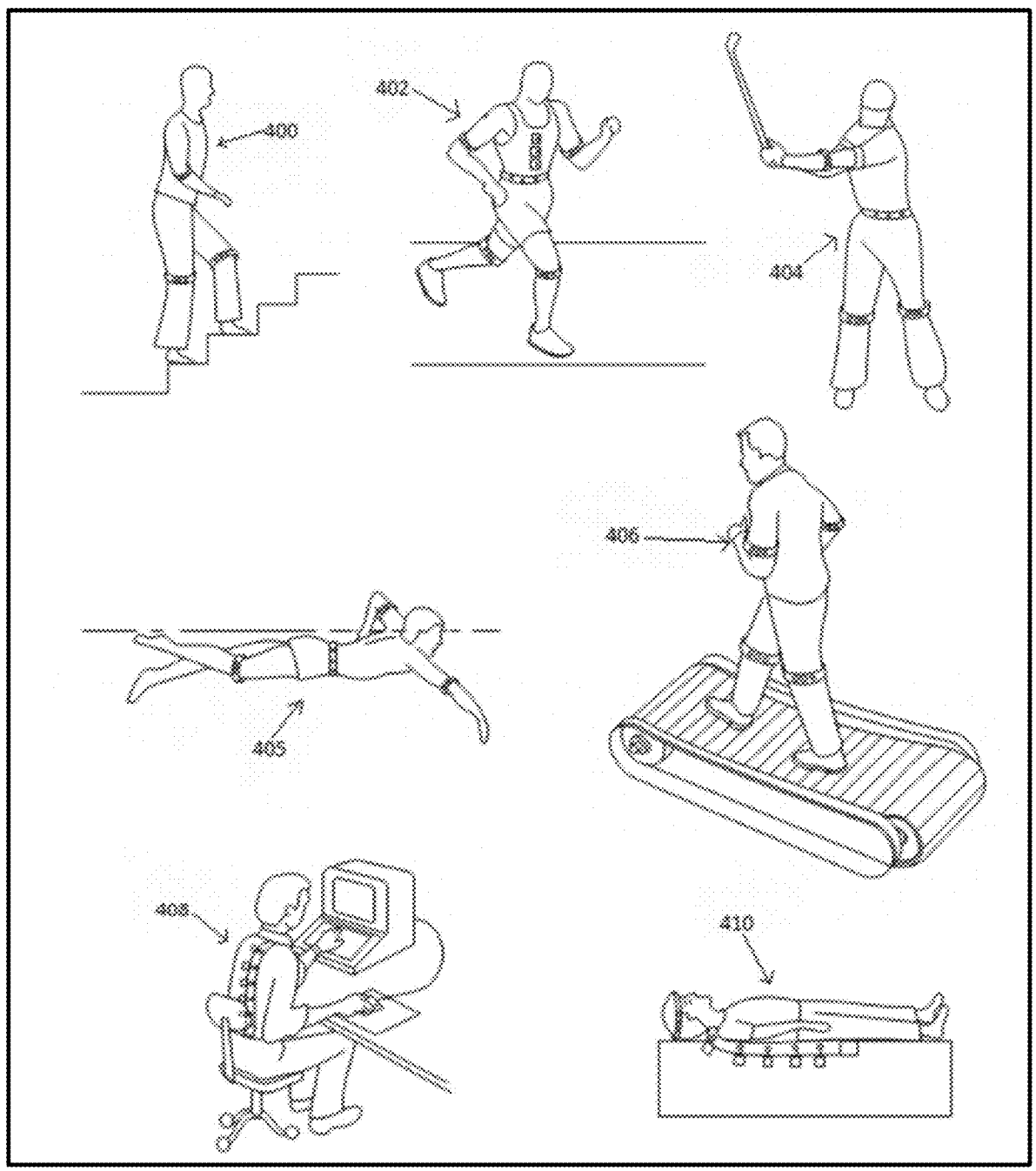
FIG. 4 illustrates exemplary joint poses that may be tracked, in accordance with embodiments of the present invention.

FIG. 4 illustrates exemplary joint poses that may be tracked, in accordance with embodiments of the present invention. In the present embodiments, joint poses may be tracked accurately to determine not just the joint positions but the overall action/intent. It may also be used to determine whether a person has had an unintentional or harmful movement of joints, such as, without limitation, falling from stairs, by tracking these poses and detecting anomalies. Embodiment 400 illustrates tracking of a person climbing stairs. The overall motion of each of the joints may be used to more accurately track the amount of calories burnt as well. Embodiment 402 illustrates tracking of joints when a person is running. In some embodiments, blood sugar level sensors may be used in conjunction with joint movement sensors to determine which type of activity keeps the blood sugar level at the ideal level.

Embodiment 404 illustrates a person playing golf being tracked. The position of joints may be very important in golf for a good swing and this information may be used to train the person and correct any errors in posture for stroke. In some embodiments, embedded actuators may provide real time feedback to joints that may be making maximum error, so that the person may adjust the stroke in real time. In some embodiments, joints movements of professional golf pros may be accurately stored using this method and analyzed. In some embodiments, this stored information may be used to retrieve the golf pro whose physical profile may be the closest fit to the user and train the user using that profile.

Embodiment 405 illustrates a person swimming and in this case the quality of the strokes may depend on the movement of the joints. In some embodiments, additional sensors which may determine when the joints touch the water and leave the water and the force with which they touch/leave the water may be measured and correlated with each other to determine if these may be optimal and the swimmer may be trained further if these are not optimal. In some embodiments, this method may be used to optimally control infinity pools to automatically adjust a rate of flow of the water to a speed with which the swimmer may be moving his joints. This may avoid accidents and may also provide for an automated change in rate of flow as the swimmer starts changing the speed of his swimming.

Embodiment 406 illustrates a person using a treadmill. The motion of the hands and legs may tracked using this method to better determine the calorie burned. In some embodiments, the treadmill may be made more predictive, so that it moves faster or slower in proportion to how the user may be moving his joints. This may prevent accidents by stopping the treadmill in case the user stops moving a joint which is supposed to be moving when the treadmill is running, for example, but not limited to, legs.

Embodiment 408 illustrates tracking of a curvature of spine as the user is operating the computer. In some embodiments, there may be embedded actuators which may give feedback to the user in case he/she may slouching or moves to an incorrect position. In some embodiments, the position of the spine may be tracked over a period of time and the user may use this information to determine which postures may be correlated with pain.

Embodiment 410 illustrates tracking of joint positions and pressures on different parts of the body as the user is sleeping and changes his/her position throughout night. In some embodiments, it may be used to determine/prevent snoring by detecting the position of different joint parts which may increase that probability and providing feedback using actuators when the body gets close to those joint positions. In some embodiments, this may be used to determine a type of bed best suited for the body based on metrics like, without limitation, minimum pressure on all joints and all joints being positioned optimally. In some embodiments, it may be used in conjunction with actuated beds to move them to preferred configurations for different joint configurations as the user moves around the bed. This may also be helpful in avoiding bed sores for people who cannot move by themselves. The method or system or device of the present invention is not limited to the above embodiments and may be used in a wide variety of cases. As a non-limiting example, it may be used to provide feedback to a head mounted Virtual Reality device about the movements of the joint so that a scene rendered can be changed accordingly. Also any combination of embodiments may be used. As a non-limiting example, where 1D, 2D or 3D treadmill like systems may be used to constrain the user in the same space for virtual reality purposes, this system may be used to provide the joint information to both the treadmill and the virtual reality system, so that the treadmill adjusts the user appropriately, while the virtual reality system moves the user correctly through the scene.

Figure 5:
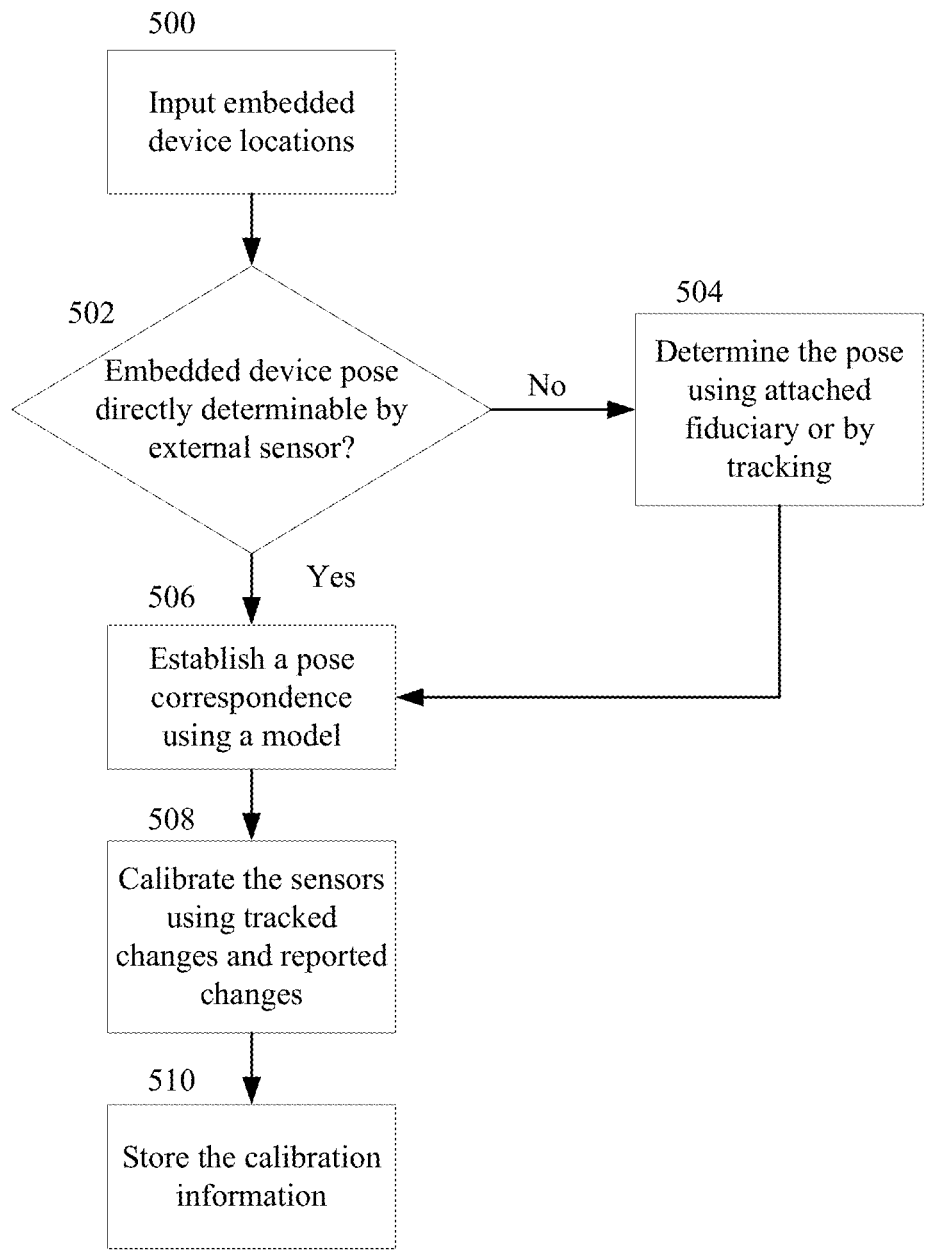
FIG. 5 illustrates an exemplary process for calibrating embedded device sensors, in accordance with an embodiment of the present invention.

FIG. 5 illustrates an exemplary process for calibrating embedded device sensors, in accordance with an embodiment of the present invention. The process starts at a step 500 with a capturing of a sequence of contemporaneously collected embedded sensor locations captured by external sensors and embedded sensor readings for a person or mechanical joint. This may be performed using, but not limited to, a depth camera (RGB-D) or a stereoscopic camera or 3D LIDAR, as described above. At a step 502, the external sensors data may be analyzed to determine the whether a particular embedded sensor may be directly observable as described above. If it may be directly observable, a pose correspondence may be established between the captured embedded device locations and also between the embedded device location and the joint location may be established in a step 506 using the model of the person/mechanical joint as described above. If it may not be directly observable, the same information may be determined by using the attached fiduciary or by tracking the relative change in embedded device pose from when its pose was externally determinable in a step 504. The sensors on the embedded devices may be calibrated in a step 508 by tracking the change in poses determined above and the change in pose reported by the sensors on the devices as the person/mechanical joint moves. This calibration information and any information obtained by showing the tracked position and taking feedback from the user may be stored on the embedded/external devices memory and/or network memory in a step 510. The process in FIG. 5 is not limited to the steps shown or the order shown. Further, as mentioned above, not all steps have to be present.

Figure 6:
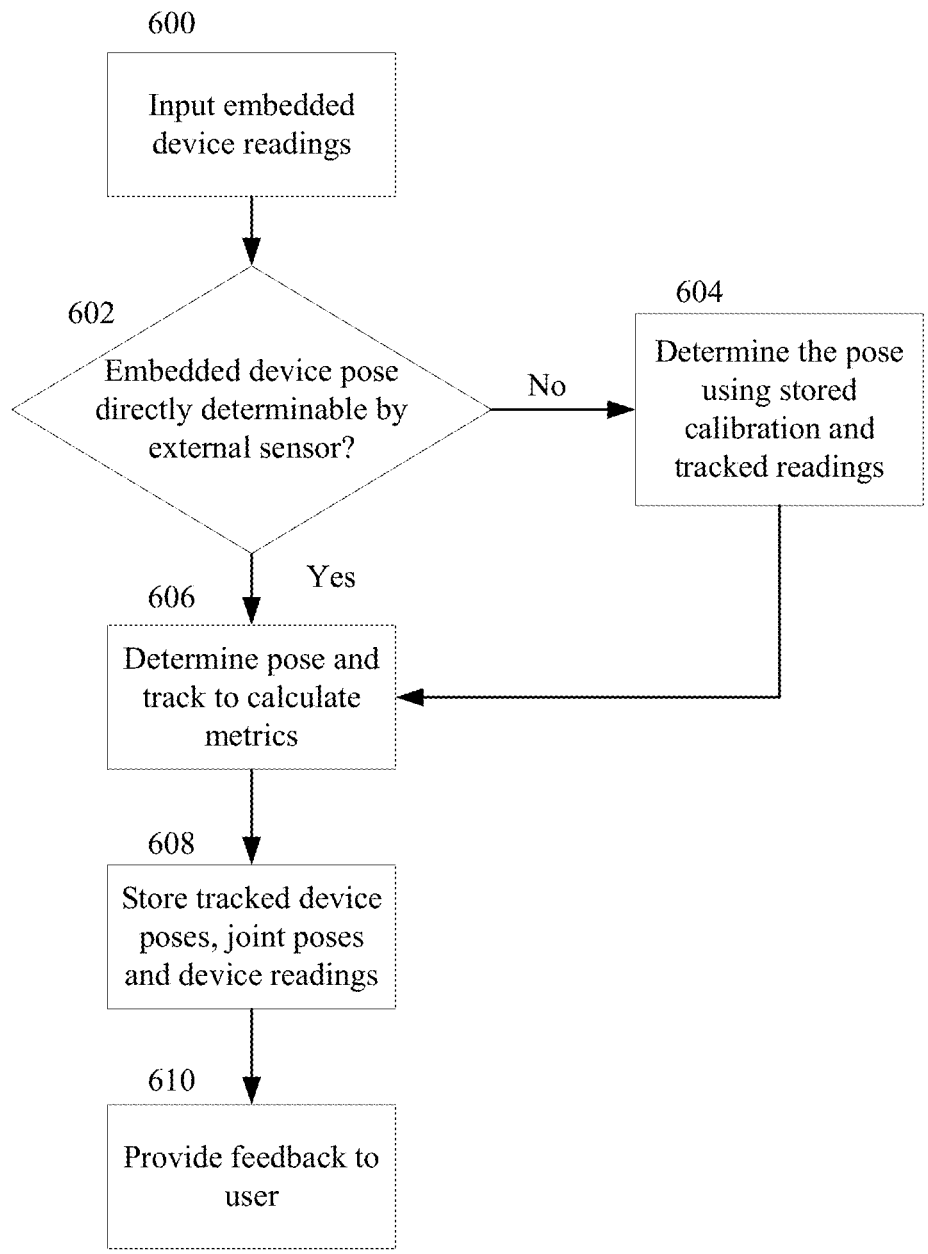
FIG. 6 illustrates an exemplary process for using calibration information to track the positions of the embedded devices, in accordance with an embodiment of the present invention.

FIG. 6 illustrates an exemplary process for using calibration information to track the positions of the embedded devices, in accordance with an embodiment of the present invention. The sensor(s) reading may be input to a computer device in a step 600. The computer device may decide whether the embedded device pose may be determinable by the external sensor(s) or not in a step 602. If it may not be determinable directly, then the stored calibration readings and tracked device sensor readings may be used to determine it by making use of the model of the person/joint as if necessary in a step 604. The joint pose may be determined by combining the joint model, the pose determined by step 602 or step 604 and/or external sensor determined pose and track this pose over time to calculate metrics like joint velocity, acceleration, etc. in a step 606. The tracked device poses and joint positions may be stored along with temporal information in a memory on device computer(s), external sensor computer(s) and or network computer in a step 608. The calculated joint position/embedded device position combined with the embedded sensor, external sensor readings and joint models may be used to provide immediate or time delayed feedback to the user using the embedded actuators/external displays or other means such as, but not limited to, personal consultation based on the gathered joint/device pose information, time and any associated data stored in the network in a step 610.

Figure 7:
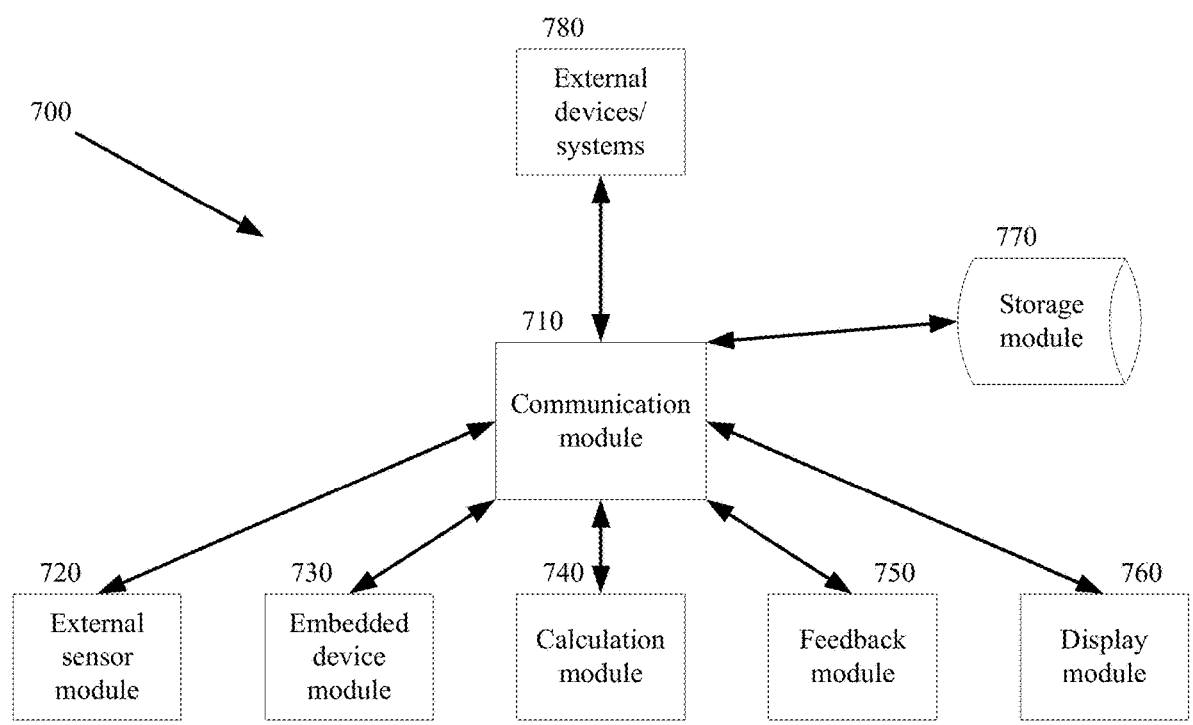
FIG. 7 illustrates an exemplary system, in accordance with an embodiment of the present invention.

FIG. 7 illustrates an exemplary system, in accordance with an embodiment of the present invention. System 700 includes, but not limited to, a communication module 710, an external sensor module 720, embedded device module 730, calculation module 740, feedback module 750, display module 760, and storage module 770. Communication module 710 may provide for communications between modules 720, 730, 740, 750, 760, 770, and other external devices/systems 780. External devices/systems 780 may include virtually any device or system that may augment the present embodiment such as, but not limited to, virtual reality systems, exercise apparatus, environmental controls, augmented reality systems, mixed reality systems, displays, glasses, wearable displays, and watches. External sensor module 720 may control various detectors configured for observing locations of the embedded devices and returning this information. Embedded device module 730 may provide receiving data from embedded devices and activation of actuators. Calculation module 740 may process real-time and stored data for calibration, modeling, tracking, analytics/metrics, and training. Feedback module 750 may control feedback to a user such as, but not limited to, tactile feedback to actuators, inputs to external devices/systems, visual and/or audio feedback, neural feedback, gustation feedback, olfactory feedback to the user. Display module 760 may control presentation of information to the user and inputs from the user. Storage module 770 may control storage and retrieval of data. In some embodiments data may be stored in a central location, either locally or remotely. In other embodiments, data storage may be distributed among several locations.

Figure 8A:
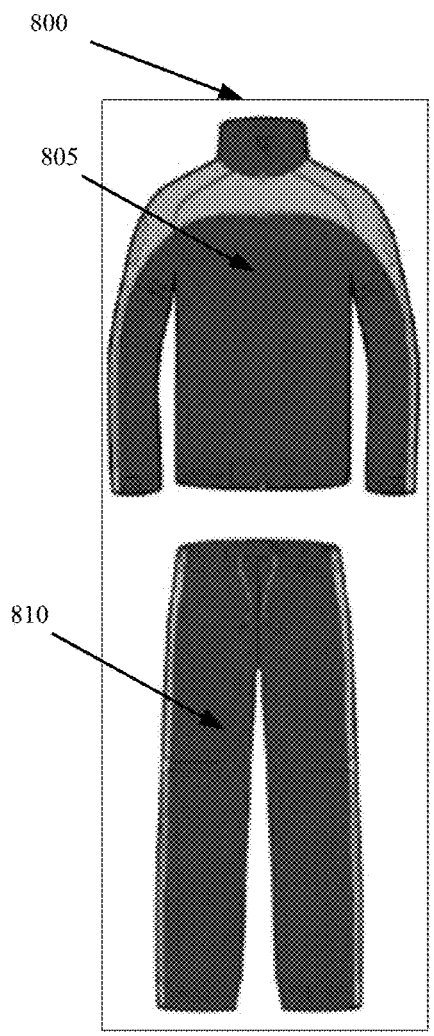
FIGS. 8A and 8b illustrate exemplary track suits, in accordance with embodiment of the present invention.
Figure 8B:
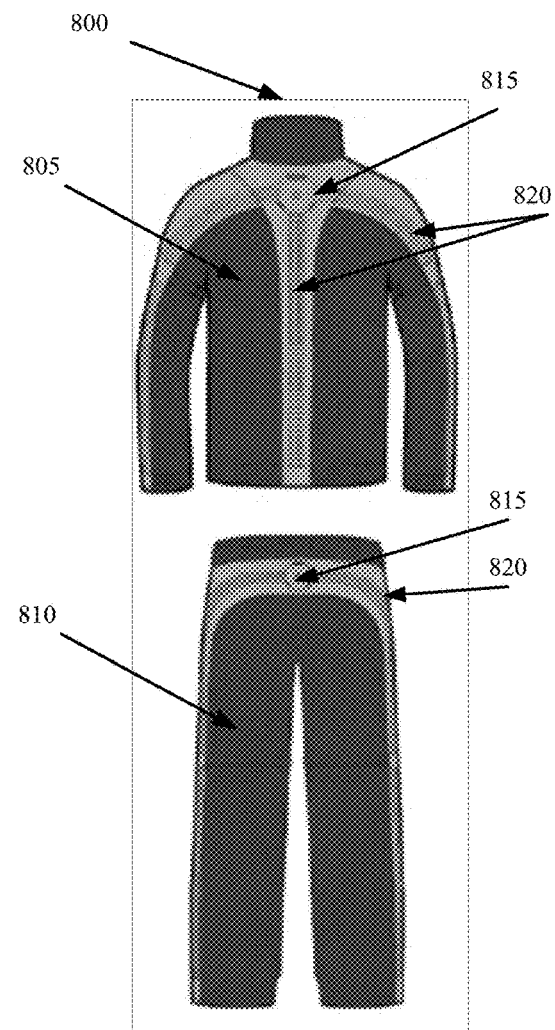

FIGS. 8A and 8b illustrate exemplary track suits, in accordance with embodiment of the present invention. FIG. 8a show an external view. FIG. 8b shows an internal view. A smart track suit 800 may include a top portion 805, a bottom portion 810, a controller 815, and embedded devices 820. Embedded devices 820 may include joint angle sensors such as, but not limited to, any combination of accelerometer, gyroscope, magnetometer and other sensors that may be used to measure the angle of the joints relative to each other or relative to any connected component. Embedded devices 820 may further include actuators. In some embodiments, track suit 800 may have conducting threads and the sensors may be placed on elastic straps or on adjustable straps so that they accurately track the joint motion. In some embodiments, sensors may be placed successively across the joints so that the pose of the entire body may be detected. In a non-limiting example, the pose of the wrist with respect to the pelvis may be detected by determining the joint angle between the spine and the shoulder and the shoulder and the arm and the arm and the forearm. Also this may allow any other sensor to be attached to these threads and since the position of the sensor on the suit may be known, the exact position of the sensor while the body is in motion may be known. This enable an interpretation of all the sensor data with context of its exact position. In a non-limiting example, it may be known that the pressure was high on lower back when the person was in a sitting position. This may allow for suggestions to the person in real time to move to a better pose and also indicate what motion he/she needs to make and also verify that the person has indeed performed that motion.

In some embodiments, the sensors may have magnets and there may be magnets underneath the threads, so that the sensors may snap into place and they may be removed easily for enabling the person to wash the cloth. In some embodiments, the main board 815 with a battery may be placed in a central location so that the power loss while supplying power to each sensor is minimized. In some embodiments, the main board 815 may have the same design of snapping magnets with threads sandwiched to allow easy removal and reattachment.

In some embodiments, the user may be wearing an augmented reality, virtual reality or mixed reality display or is viewing it on an external display. The motion of the user in the real world may be tracked using the joint angles and the accelerometer, gyroscope, magnetometer readings. In a non-limiting example, a 3 axis accelerometer may determine whether the user is jumping up or down or moving forward. This may be used in combination with the knowledge of the location of that sensor in the track suit to determine the overall motion of the person in the real world. This motion may be mirrored in the virtual world, by having an 3D avatar whose body motions mimic the motion of the user. This may be used to enable the user to point and select objects in the virtual world by tracking the joint positions of his/her elbows, forearms and the heading of the torso. Also this may enable the user to touch objects in the virtual/augmented world as he moves around in the real world. It may also enable the user to navigate around the virtual/augmented world scenes by using the body motion as a control.

In some embodiments, since the sensors may all be embedded on the user and move with him/her, it may enable the user to travel virtually any distance in the real world and have his/her motion tracked. This may not be possible with an external sensor. Also external sensors may not work in all places, for example, without limitation, in low visibility environments, some sensors like ToF may only work indoors, others may only work within a limited range etc. This may also enable the user to play games in the augmented reality world like, without limitation, golf, tennis, cricket, etc. and get real time feedback about their motion and well as training to improve their skills in the augmented world. In some embodiments, they may also capture their performance in the real world by wearing this suit to a golf course or tennis match for example, without limitation, and review their actions in the virtual/augmented world. In some embodiments, they may even play matches with other people who may be using virtual displays where part each player's body movement may be used to drive a shared augmented or virtual world. As each person moves in the real world, their 3D avatars may move in the combined virtual world and interact with the objects in the combined world. In a non-limiting example, a virtual tennis court may be created and each person's avatar may be on one side of the tennis court and their body actions may create a virtual game. Similarly, without limitation, sword fighting, golf, light saber fighting, billiards and any game which requires bodily motion may be enabled for augmented, virtual reality by this type of body. In some embodiments, the user may train in the virtual world and use that training directly in the real world, since there may be direct correspondence between those motions. In some embodiments, the user may record their actions in the real world using this suit and review them either personally or with their team and even suggest changes/improvements in the virtual world and visualize those improvements/changes. In some embodiments, additional external sensors may capture the actual ball motion, the environmental factors like, without limitation, humidity, air flow, etc. and replay it along with their body joint motion so that they may review their performance. In some embodiments, multiple persons wearing suits may be involved in group performances and each embedded sensor may correlate with the external sensor and other embedded sensors to capture the entire group performance and reproduce it in the virtual world.

In some embodiments, there may be embedded output devices like RGB LEDs, sounds or vibration devices on these tracksuits which may give real time feedback and training to the user as to how to achieve their goal better. In a non-limiting example, in tennis the combination of external sensor and embedded sensor may detect that the user is consistently moving his shoulder a little lower resulting in the ball hitting the net. Thus next time the embedded sensor determines the user may be about to make the same mistake, it may buzz or turn red or vibrate at the shoulder to indicate the user needs to correct his shoulder position with respect to other joints to make sure he/she doesn't hit the net. In another non-limiting example, in yoga, there may be a set of desired 3D avatar poses for each asana, yoga pose, and the feedback may be used to nudge the user to move each of the joints to the desire pose.

In some embodiments, the motion of a trainer for different types of motions, for example, without limitation, different golf shots may be captured accurately with not just joint position, but also the joint velocity, acceleration information and the real motion of the ball or desired output may be tracked using an external sensor. These two may be correlated and a model developed to extrapolate all types of body motions and the resulting changes in the world such as, without limitation, motion of the ball. This capture may be done in different settings such as, but not limited to, different wind conditions and those settings may be also simulated either individually or as a combination such as, but not limited to, wind plus high humidity.

In some embodiments, the joint position, velocity and acceleration may be used to tele-operate a device either in the virtual world or the real world. In a non-limiting example, it may be used to fly a virtual or real drone by moving the arms up and down or turn the direction of the virtual or real airplane by turning the body around. In some embodiments, it may be used to control anthropomorphic real or virtual robots either with the whole body or individual body parts. In a n0n-limiting example when the human moves the hand up, the real or virtual robot may also move its hand up. There may be any kind of transformation between the two motions (the actual tracked joint motion and the corresponding virtual or real device motion), for example, without limitation, scaling, mirroring, rotation etc.

Figure 9:
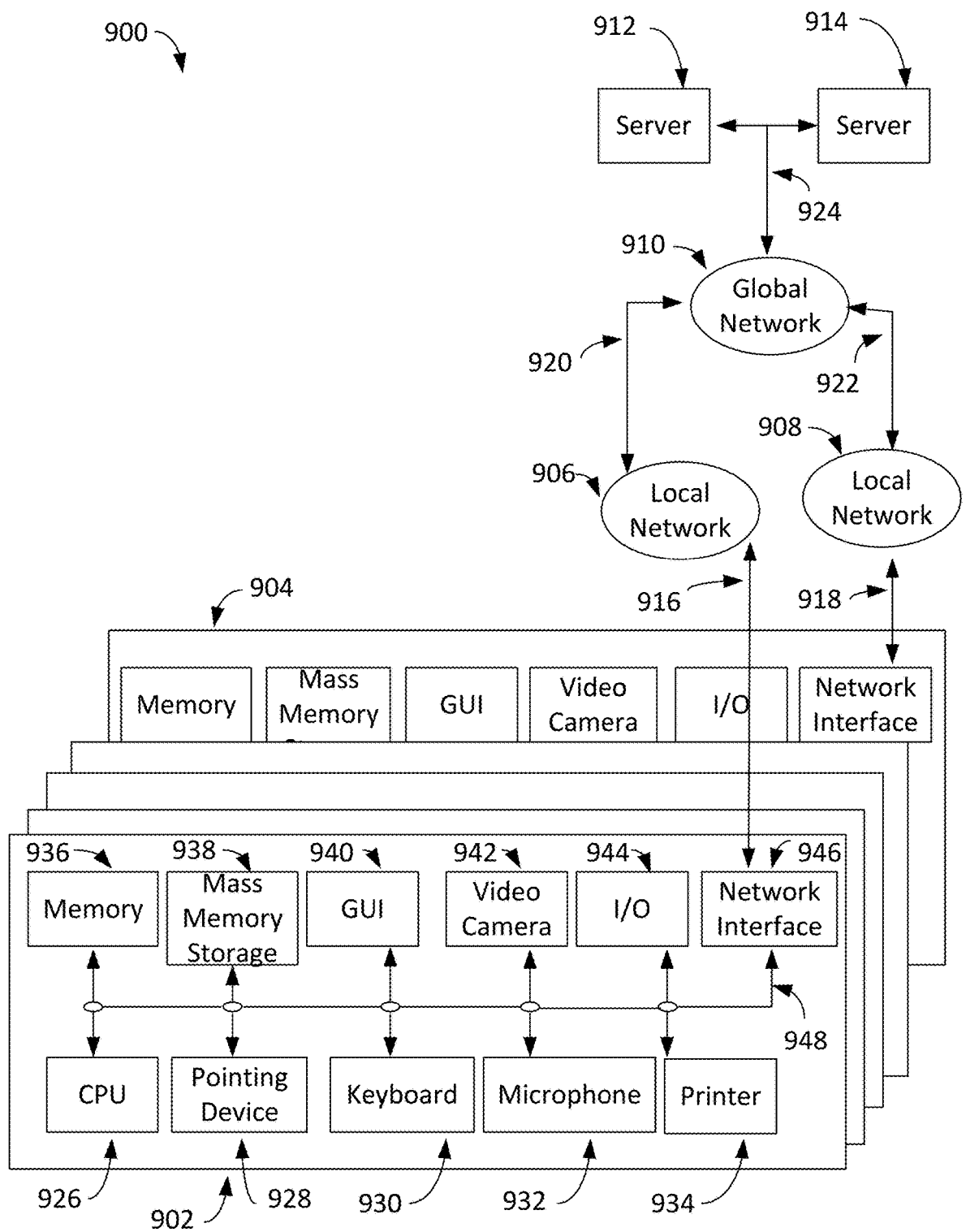
FIG. 9 is a block diagram depicting an exemplary client/server system which may be used by an exemplary web-enabled/networked embodiment of the present invention.

FIG. 9 is a block diagram depicting an exemplary client/server system which may be used by an exemplary web-enabled/networked embodiment of the present invention.

A communication system 900 includes a multiplicity of clients with a sampling of clients denoted as a client 902 and a client 904, a multiplicity of local networks with a sampling of networks denoted as a local network 906 and a local network 908, a global network 910 and a multiplicity of servers with a sampling of servers denoted as a server 912 and a server 914.

Client 902 may communicate bi-directionally with local network 906 via a communication channel 916. Client 904 may communicate bi-directionally with local network 908 via a communication channel 918. Local network 906 may communicate bi-directionally with global network 910 via a communication channel 920. Local network 908 may communicate bi-directionally with global network 910 via a communication channel 922. Global network 910 may communicate bi-directionally with server 912 and server 914 via a communication channel 924. Server 912 and server 914 may communicate bi-directionally with each other via communication channel 924. Furthermore, clients 902, 904, local networks 906, 908, global network 910 and servers 912, 914 may each communicate bi-directionally with each other.

In one embodiment, global network 910 may operate as the Internet. It will be understood by those skilled in the art that communication system 900 may take many different forms. Non-limiting examples of forms for communication system 900 include local area networks (LANs), wide area networks (WANs), wired telephone networks, wireless networks, or any other network supporting data communication between respective entities.

Clients 902 and 904 may take many different forms. Non-limiting examples of clients 902 and 904 include personal computers, personal digital assistants (PDAs), cellular phones and smartphones.

Client 902 includes a CPU 926, a pointing device 928, a keyboard 930, a microphone 932, a printer 934, a memory 936, a mass memory storage 938, a GUI 940, a video camera 942, an input/output interface 944 and a network interface 946.

CPU 926, pointing device 928, keyboard 930, microphone 932, printer 934, memory 936, mass memory storage 938, GUI 940, video camera 942, input/output interface 944 and network interface 946 may communicate in a unidirectional manner or a bi-directional manner with each other via a communication channel 948. Communication channel 948 may be configured as a single communication channel or a multiplicity of communication channels.

CPU 926 may be comprised of a single processor or multiple processors. CPU 926 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 936 is used typically to transfer data and instructions to CPU 926 in a bi-directional manner. Memory 936, as discussed previously, may include any suitable computer-readable media, intended for data storage, such as those described above excluding any wired or wireless transmissions unless specifically noted. Mass memory storage 938 may also be coupled bi-directionally to CPU 926 and provides additional data storage capacity and may include any of the computer-readable media described above. Mass memory storage 938 may be used to store programs, data and the like and is typically a secondary storage medium such as a hard disk. It will be appreciated that the information retained within mass memory storage 938, may, in appropriate cases, be incorporated in standard fashion as part of memory 936 as virtual memory.

CPU 926 may be coupled to GUI 940. GUI 940 enables a user to view the operation of computer operating system and software. CPU 926 may be coupled to pointing device 928. Non-limiting examples of pointing device 928 include computer mouse, trackball and touchpad. Pointing device 928 enables a user with the capability to maneuver a computer cursor about the viewing area of GUI 940 and select areas or features in the viewing area of GUI 940. CPU 926 may be coupled to keyboard 930. Keyboard 930 enables a user with the capability to input alphanumeric textual information to CPU 926. CPU 926 may be coupled to microphone 932. Microphone 932 enables audio produced by a user to be recorded, processed and communicated by CPU 926. CPU 926 may be connected to printer 934. Printer 934 enables a user with the capability to print information to a sheet of paper. CPU 926 may be connected to video camera 942. Video camera 942 enables video produced or captured by user to be recorded, processed and communicated by CPU 926.

CPU 926 may also be coupled to input/output interface 944 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 926 optionally may be coupled to network interface 946 which enables communication with an external device such as a database or a computer or telecommunications or internet network using an external connection shown generally as communication channel 916, which may be implemented as a hardwired or wireless communications link using suitable conventional technologies. With such a connection, CPU 926 might receive information from the network, or might output information to a network in the course of performing the method steps described in the teachings of the present invention.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6). In some embodiments, the methods and/or system components which may be located and/or performed remotely include, without limitation:

It is noted that according to USA law, all claims must be set forth as a coherent, cooperating set of limitations that work in functional combination to achieve a useful result as a whole. Accordingly, for any claim having functional limitations interpreted under 35 USC § 112 (6) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6) is/(are) dependent on one or more remote servers located outside the USA, it is intended that each such recited function under 35 USC § 112 (6) is to be interpreted as the function of the local system receiving the remotely generated information required by a locally implemented claim limitation, wherein the structures and or steps which enable, and breath life into the expression of such functions claimed under 35 USC § 112 (6) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present application, and "35 USC § 112 (6)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing multi-joint tracking according to the present invention will be apparent to those skilled in the art. Various aspects of the invention have been described above by way of illustration, and the specific embodiments disclosed are not intended to limit the invention to the particular forms disclosed. The particular implementation of the multi-joint tracking may vary depending upon the particular context or application. By way of example, and not limitation, the multi-joint tracking described in the foregoing were principally directed to multi joint tracking combining embedded sensors and external sensor implementations; however, similar techniques may instead be applied to robotic control, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A computer-implemented multi joint tracking method performed by one or more processors, the method comprising:
    assigning at least a first location of at least one embedded device, the at least one embedded device comprising at least one sensor and being associated with at least one joint capable of movement, the first location being captured by the at least one sensor;
    assigning at least a second location of the at least one embedded device, the second location being captured by observation of the at least one embedded device by at least one external sensor, wherein the at least one external sensor tracks motion of the at least one joint with respect to an external reference, wherein the at least one external sensor is a Red Green Blue Depth (RGB-D) sensor;
    establishing a pose correspondence between the at least first location and the at least second location using a model of the at least one joint to extract relative information between the at least one embedded device at the at least first location and the at least one embedded device at the at least second location;
    calibrating the at least one sensor of the at least one embedded device by tracking a change in a pose captured by the at least one external sensor and a change in the pose, captured by the at least one sensor of the at least one embedded device as the at least one joint moves in order to obtain at least one calibrated sensor of the at least one embedded device;

determining that each of the at least one calibrated sensor is not observed by the at least one external sensor;

inferring a relative position of the at least one calibrated sensor and the at least one joint, in real-time, using the model of the at least one joint based on the determination that each of the at least one calibrated sensor is not observed by the at least one external sensor, thereby tracking overall position and motion of the at least one joint;

performing at least one of:
one or more actions on an external object based on inference of the relative position of the at least one calibrated sensor and the at least one joint, as the at least one joint moves; and
providing feedback to a user at least in part based on inference of the relative position of the at least one calibrated sensor and the at least one joint as the at least one joint moves by activating an actuator of the at least one embedded device.

2. The method as recited in claim 1, further comprising the steps of:
capturing a plurality of first locations reported by the at least one sensor during movement of the at least one joint;
capturing a plurality of second locations reported by the at least one external sensor during movement of the at least one joint;
determining a plurality of joint poses from the plurality of first locations, the plurality of second locations and the model; and
calculating metrics using the plurality of joint poses.

3. The method as recited in claim 2, further comprising the step of storing tracked data at least comprising, the plurality of first locations, the plurality of second locations, the plurality of joint poses, and the metrics.

4. The method as recited in claim 1, further comprising the step of generating a display at least in part based on the feedback.

5. The method as recited in claim 1, in which the at least one joint is associated with a user.

6. The method as recited in claim 1, in which the at least one joint is associated with a spine.

7. A non-transitory computer-readable storage medium with an executable program stored thereon, wherein the program instructs one or more processors to perform a multi joint tracking method, the method comprising:
steps for assigning a first location of an embedded device captured by a sensor of the embedded device, the embedded device being associated with at least one joint;
steps for assigning a second location of the embedded device captured by observation by an external sensor, wherein the external sensor tracks motion of the at least one joint with respect to an external reference, wherein the external sensor is a Red Green Blue Depth (RGB-D) sensor;
steps for establishing a pose correspondence between the first location and the second location to extract relative information between the embedded device at the first location and the embedded device at the second location;
steps for calibrating the sensor of the embedded device by tracking a change in a pose captured by the external sensor and a change in the pose captured by the sensor of the embedded device as the at least one joint moves in order to obtain a calibrated sensor of the embedded device;
steps for determining that the calibrated sensor is not observed by the at least one external sensor;
steps for inferring a relative position of the calibrated sensor and the at least one joint, in real-time, using the model of the at least one joint based on the determination that the calibrated sensor is not observed by the external sensor, thereby tracking overall position and motion of the at least one joint;
steps for performing at least one of:
one or more actions on an external object based on inference of the relative position of the calibrated sensor and the at least one joint, as the at least one joint moves; and
providing feedback to a user at least in part based on inference of the relative position of the calibrated sensor and the at least one joint as the at least one joint moves by activating an actuator of the embedded device.

8. The method as recited in claim 7, further comprising:
steps for capturing a plurality of first locations during movement of the joint;
steps for capturing a plurality of second locations during movement of the joint;
steps for determining a plurality of joint poses; and steps for calculating metrics.

9. The method as recited in claim 8, further comprising steps for storing tracked data.

10. The method as recited in claim 7, further comprising steps for generating a display based on the feedback.

11. A non-transitory computer-readable storage medium with an executable program stored thereon, wherein the program instructs one or more processors to perform the steps of:
assigning at least a first location of at least one embedded device, the at least one embedded device comprising at least one sensor and being associated with at least one joint capable of movement, the at least first location being captured by the at least one sensor;
assigning at least a second location of the at least one embedded device, the at least second location being captured by observation of the at least one embedded device by at least one external sensor, wherein the at least one external sensor tracks motion of the at least one joint with respect to an external reference, wherein the at least one external sensor is a Red Green Blue-Depth (RGB-D) sensor;
establishing a pose correspondence between the at least first location and the at least second location using a model of the at least one joint to extract relative information between the at least one embedded device at the at least first location and the at least one embedded device at the at least second location;
calibrating the at least one sensor of the at least one embedded device by tracking a change in a pose captured by the at least one external sensor and a change in the pose captured by the at least one sensor of the at least one embedded device as the at least one joint moves in order to obtain at least one calibrated sensor of the at least one embedded device;
determining that each of the at least one calibrated sensor is not observed by the at least one external sensor;
inferring a relative position of the at least one calibrated sensor and the at least one joint, in real-time, using the model of the at least one joint based on the determination that each of the at least one calibrated sensor is not observed by the at least one external sensor, thereby tracking overall position and motion of at least one joint;

performing at least one of:

one or more actions on an external object based on inference of the relative position of the at least one calibrated sensor and the at least one joint as the at least one joint moves; and providing feedback to a user at least in part based on inference of the relative position of the at least one calibrated sensor and the at least one joint as the at least one joint moves by activating an actuator of the at least one embedded device.

12. The program instructing the one or more processors as recited in claim 11, further comprising the steps of:

capturing a plurality of first locations reported by the at least one sensor during movement of the at least one joint;

capturing a plurality of second locations reported by the at least one external sensor during movement of the at least one joint; determining a plurality of joint poses from the plurality of first locations, the plurality of second locations and the model; and calculating metrics using the plurality of joint poses.

13. The program instructing the one or more processors as recited in claim 12, further comprising the step of storing tracked data at least comprising, the plurality of first locations, the plurality of second locations, the plurality of joint poses, and the metrics.

14. The program instructing the one or more processors as recited in claim 11, further comprising the step of generating a display at least in part based on the feedback.

* * * * *